(12) United States Patent
Johnson

(10) Patent No.: US 8,500,667 B2
(45) Date of Patent: Aug. 6, 2013

(54) CREVICE COLLAR

(75) Inventor: Katherine Johnson, Spencer, IA (US)

(73) Assignee: Brownmed, Inc., Spirit Lake, IA (US)

( * ) Notice: Subject to any disclaimer, the term of this patent is extended or adjusted under 35 U.S.C. 154(b) by 948 days.

(21) Appl. No.: 12/241,258

(22) Filed: Sep. 30, 2008

(65) Prior Publication Data

US 2010/0081980 A1    Apr. 1, 2010

(51) Int. Cl.
*A61F 5/00*    (2006.01)

(52) U.S. Cl.
USPC .............................................. 602/18; 602/75

(58) Field of Classification Search
USPC ........ 602/18, 75, 20–23, 60–62, 74, 76; 2/16, 2/22; 606/201, 204, 204.35; 128/112.1, 95.1, 128/99.1, 100.1, 892
See application file for complete search history.

(56) References Cited

U.S. PATENT DOCUMENTS

| | | | | |
|---|---|---|---|---|
| 4,223,095 A | * | 9/1980 | Esser et al. | 521/55 |
| 4,991,573 A | * | 2/1991 | Miller | 602/19 |
| 6,254,554 B1 | * | 7/2001 | Turtzo | 601/134 |

\* cited by examiner

*Primary Examiner* — Patricia Bianco
*Assistant Examiner* — Camtu Nguyen
(74) *Attorney, Agent, or Firm* — McKee, Voorhees & Sease, P.L.C.

(57) ABSTRACT

A device for treatment of limbs affected with Lymphedema. The device is a crevice collar which fits into depressed areas and crevices created by over-hanging lobules and protrusions of tissue so that the tissue may be comfortably wrapped with a pressure wrap with exacerbating sores and crevice areas in the skin caused by the Lymphedema.

1 Claim, 2 Drawing Sheets

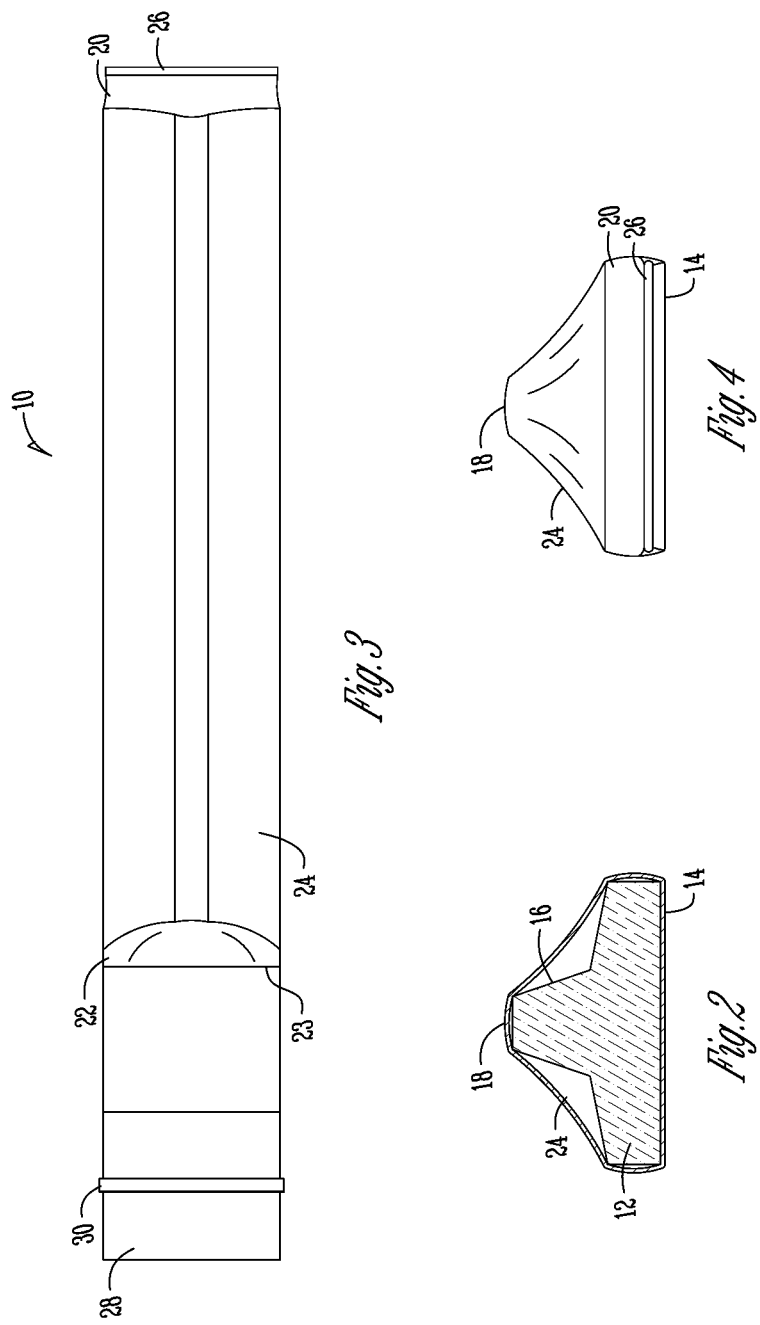

CREVICE COLLAR

FIELD OF THE INVENTION

The field of this invention relates to a device to assist patients in comfort level and effectiveness when limbs suffering from Lymphedema are wrapped with compression wraps.

BACKGROUND OF THE INVENTION

Lymphedema refers to swelling that occurs most often in a patent's arms or legs. It may affect just one arm or leg but sometimes Lymphedema can involve both arms or legs. It involves swelling which occurs when there is blockage in the lymphatic system, preventing the lymph fluid in arms or legs from draining adequately. As the fluid accumulates, the swelling continues. Swelling can range from mild, hardly noticeable changes in size of the limb to extreme swelling that may affect the use of the affected limb, in which case skin folds may occur that cause skin irritation, sores and discomfort, and further complication in lymph drainage. It is also often accompanied by a feeling of heaviness or tightness in the limb, restricted range of motion and recurring infections.

Lymphedema can occur as so-called primary Lymphedema resulting from problems with the natural development lymph vessels in the body, or more commonly resulting from secondary causes incident to surgery, radiation treatment for cancer, infection, and injury that damages the lymph nodes or the lymph vessels.

A normal lymphatic system routinely removes protein-rich fluid. When it becomes compromised, these fluids accumulate in the interstitial space. It is caused by impairment of the lymphatic system, which can be primary, i.e. congenital or secondary, i.e. due to injury. The primary symptom is swelling from the accumulated fluid, but chronic Lymphedema produces a fibrotic and darkened skin, and an increased risk of infection because the protein rich environment is favorable to bacterial growth.

One common disease condition that causes Lymphedema is a breast cancer treatment wherein lymph nodes are sacrificed and edema of the arm frequently occurs. One frequent treatment of Lymphedema is compression wraps that typically, after moisturizing the skin, a therapist then applies the pressure wrap to force the collected fluid to drain. Wrapping can often become a daily function. And, when the patient has overhanging lobules and protrusions of tissue that create crevices, the compression wrap often goes into the area causing it to either irritate the skin, or lose its effectiveness, or both. It can be seen therefore there is a continuing need to provide for a device which allows effective use of compression wraps with the limbs of patients suffering from Lymphedema. This invention has as its primary objective providing such a device and a method of using the device.

Other means of accomplishing the above primary objective and solving of the need mentioned above will become apparent from the detailed description of the invention which follows hereinafter.

Wrap construction here shown is illustrative only. Put another way the configuration can be changed and still achieve the invention results, i.e., an effective crevice collar for use in conjunction with Lymphedema compression wraps.

BRIEF SUMMARY OF THE INVENTION

A device for treatment of limbs affected with Lymphedema. The device is a crevice collar which fits into depressed areas and crevices created by over-hanging lobules and protrusions of tissue so that the tissue may be comfortably wrapped with a pressure wrap without exacerbating sores and crevice areas in the skin, caused by the Lymphedema.

BRIEF DESCRIPTION OF THE DRAWINGS

FIG. 2 is a sectional view along line 2-2 of FIG. 1.
FIG. 3 is a plan view of the device of FIG. 1 showing the upper surface.
FIG. 4 is an end view of the end opposite end having the rollup stretch band sewn to it.

DETAILED DESCRIPTION OF THE PREFERRED EMBODIMENT

Figure 1:
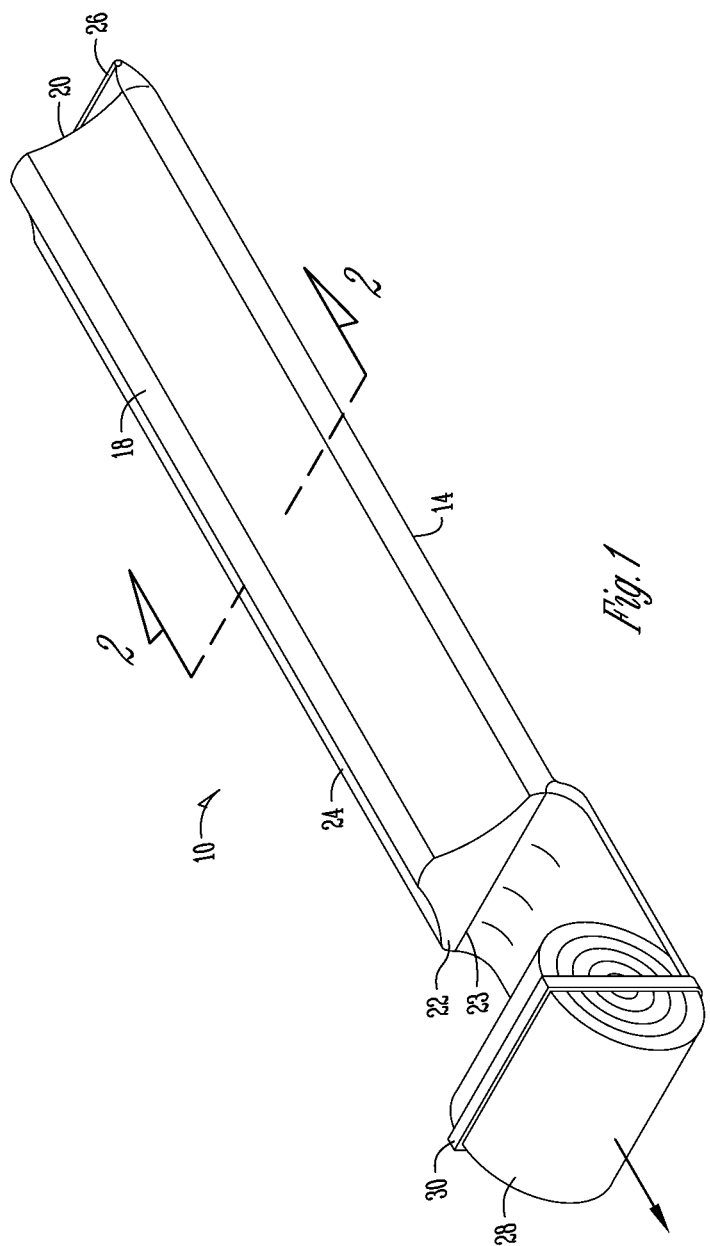
FIG. 1 is a perspective view of the crevice collar device of the present invention.

Looking at FIG. 1, crevice collar 10 is shown. It generally is comprised of a strip of cushion material 12 which is elongated and has a generally flat lower surface 14 and a ridged upper surface 16 culminating in a ridge or rib 18 at the apex best shown in cross-sectional view shown in FIG. 2. The cushion material may be polymeric material which can be natural rubber or synthetic polymer, open or closed cell and can be a foam material such as polyurethane. It is preferred for patient's safety that the cushion material is flame resistant. The cushion material 12 in addition to having the previously defined lower surface 14 and upper surface 16 also has opposing first and second ends 20 and 22. A strip of cushion material 12 is covered with a stockinette 24. Stockinette 24 can be made of any suitable stretch or pull hosiery-like material, natural or synthetic fibers including cotton, rayon, nylon and other polymeric base materials such as polypropylene, ethylene, etc., either woven or nonwoven but preferably woven. End 20 is sewn shut as indicated by end seam 26. The opposite of the first end 20 is the second end 22. Sewn (see seam 23) to the second end 22 is a rollup compression bandage 28. Compression bandage 28 may be held in rolled or stored condition by a rubber band 30.

One preferred material for the cushion material has the following properties outlined in Table I.

TABLE I

| Product: | | |
|---|---|---|
| Physical Property | Value | Test Method |
| Color | White | |
| Density (lbs/ft3) | 1.7-1.9 | ASTM D-3574-01 |
| Indent Force Deflection @ 25% | 81-99 | ASTM D-3574-01 |
| Compression Set at 50% comp.(%) | 10 | ASTM D-3574-01 |
| Tensile Strength (psi) | 10 | ASTM D-3574-01 |
| Tear Strength (lbs/lin inch) | 1.25 | ASTM D-3574-01 |
| Elongation (%) | 125 | ASTM D-3574-01 |
| Flame Resistance | N/A | |

A crevice collar may be used with limbs of patients suffering from Lymphedema in the following manner. The therapist first determines the correct size of crevice collar needed, i.e., how long of a strip of the cushion material 12 is needed. It is convenient to provide three sizes 12, 16 and 24 inch lengths. The skin is moisturized and the therapist applies the crevice collar 10 by laying the wedged side of the collar (see rib 18 directed towards the skin) such that the flat side lower surface 14 is flush with the skin and the ridge is in the nest area or crevice created by overhanging lobules and protrusions of tissue. Crevice collar 10 is fitted circumferentially into the entire crevice and the collar is secured in place with the compression bandage 20 sewn to an end. When the crevice collar application is completed, the patient is then wrapped with a normal compression wrap or garment over the crevice collar 10. In this way the compression wrap causes the Lymphedema swelling to be controlled and allows the excess fluid to drain. Because of the crevice collar and the compression wrap over it (not shown) the compression wrap stays secure and does not become unwrapped or lose its compression effectiveness, ensuring that rewrapping is not necessary. It can be seen the crevice collar 10 is designed to conveniently fit into crevices in the skin, the stockinette is comfortable and the wrap allows quick application for a smooth surface so that the overall compression wrap surrounding it maintains its effectiveness to cause fluid drainage away from appendage that can be absorbed by the body.

Therefore, it can be seen that the crevice collar 10 accomplishes the stated objectives of the invention.

What is claimed is:

1. A method of wrapping a limb suffering from Lymphedema, comprising:

providing a crevice collar having a strip of cushion material, having a length, first and second ends, a generally flat lower surface, and a ridged upper surface, with a pair of oppositely disposed sidewalk each extending from the flat lower surface inwardly and upwardly to said ridged upper surface;

a cloth like stockinette covering surrounding the entire strip of cushion material; and a roll up stretch band attached to at least one of said first and second ends;

placing the rigid upper surface in the crevice of any skin fold caused by the Lymphedema and wrapping the limb with said stretch hand to secure the crevice collar in position with its lower flat surface exposed; and wrapping said stretch band around the limb and over the exposed generally flat lower surface of the crevice collar.

\* \* \* \* \*

UNITED STATES PATENT AND TRADEMARK OFFICE
CERTIFICATE OF CORRECTION

PATENT NO. : 8,500,667 B2
APPLICATION NO. : 12/241258
DATED : August 6, 2013
INVENTOR(S) : Johnson Page 1 of 1

It is certified that error appears in the above-identified patent and that said Letters Patent is hereby corrected as shown below:

In the Claims

<u>Col. 4, Claim 1, Line 4:</u>
DELETE after disposed "sidewalk"
ADD after disposed --sidewalls--

<u>Col. 4, Claim 1, Line 13:</u>
DELETE after stretch "hand"
ADD after stretch --band--

Signed and Sealed this
First Day of October, 2013

Teresa Stanek Rea
*Deputy Director of the United States Patent and Trademark Office*